US008659603B2

(12) United States Patent
Song et al.

(10) Patent No.: US 8,659,603 B2
(45) Date of Patent: Feb. 25, 2014

(54) SYSTEM AND METHOD FOR CENTER POINT TRAJECTORY MAPPING

(75) Inventors: Ting Song, Rockville, MD (US); Vincent B. Ho, N. Bethesda, MD (US)

(73) Assignees: General Electric Company, Schenectady, NY (US); The Henry M. Jackson Foundation for the Advancement of Military Medicine, Inc., Rockville, MD (US)

( * ) Notice: Subject to any disclaimer, the term of this patent is extended or adjusted under 35 U.S.C. 154(b) by 1091 days.

(21) Appl. No.: 12/415,538

(22) Filed: Mar. 31, 2009

(65) Prior Publication Data

US 2010/0245360 A1 Sep. 30, 2010

(51) Int. Cl.
*G06T 11/20* (2006.01)
*G06T 11/40* (2006.01)

(52) U.S. Cl.
CPC .......... *G06T 11/206* (2013.01); *G06T 11/203* (2013.01); *G06T 11/40* (2013.01)
USPC ............... 345/440; 345/440.1; 345/440.2; 345/441; 345/442; 345/443

(58) Field of Classification Search
CPC ...... G06T 11/206; G06T 11/203; G06T 11/40
USPC ................. 345/440–442; 382/128–132
See application file for complete search history.

(56) References Cited

U.S. PATENT DOCUMENTS

| 6,208,749 B1 * | 3/2001 | Gutkowicz-Krusin et al. ............... 382/128 |
| 6,614,919 B1 | 9/2003 | Suzaki et al. |
| 7,876,938 B2 * | 1/2011 | Huang et al. .................. 382/128 |
| 2004/0087853 A1 | 5/2004 | Fujisawa |
| 2008/0159610 A1 | 7/2008 | Haas et al. |
| 2008/0170763 A1 | 7/2008 | Begelman et al. |
| 2008/0214907 A1 * | 9/2008 | Gutkowicz-Krusin et al. ............... 600/306 |
| 2009/0300692 A1 * | 12/2009 | Mavlankar et al. ............. 725/94 |
| 2010/0027865 A1 * | 2/2010 | Wels et al. ................... 382/131 |

FOREIGN PATENT DOCUMENTS

| JP | 2005028123 A | 2/2005 |
| WO | 2005/074804 A1 | 8/2005 |
| WO | 2006/137016 A1 | 12/2006 |
| WO | 2008/065611 A2 | 6/2008 |

OTHER PUBLICATIONS

G.S. Mageras, A. Pevsner and E.D. Yorke, et al. "Measurement of lung tumor motion using respiration-correlated CT", Int J Radiat Oncol Biol Phys, vol. 60 (2004), pp. 933-941.*

(Continued)

*Primary Examiner* — Jin-Cheng Wang
(74) *Attorney, Agent, or Firm* — Ziolkowski Patent Solutions Group, SC

(57) ABSTRACT

A system and method for center point trajectory mapping includes a computer readable storage medium having stored thereon a computer program comprises instructions, which when executed by a computer, cause the computer to acquire a first plurality of images, each image comprising a masked portion. The instructions also cause the computer to locate a center point of the masked portion in each of the plurality of images and to plot a map based on variances in position of the center points from each other. The instructions further cause the computer to display the map on a display.

20 Claims, 9 Drawing Sheets

(56) References Cited

OTHER PUBLICATIONS

JD Pearlman, RD Hogan, PS Wiske, TD Franklin and AE Weyman, Echocardiographic definition of the left ventricular centroid. I. Analysis of methods for centroid calculation from a single tomogram. J Am Coll Cardiol, 16 (1990), pp. 986-992.*
A. E. Brito, E. Whittenberger, and S. D. Cabrera, Segmentation Strategies with Multiple Analysis for an SMD Object Recognition System, Proceedings of Southwest Symposium on Image Analysis and Interpretation, pp. 59-64, Tucson AZ., Apr. 1998.*
L.M. Fletcher-Heath, L.O. Hall and D.B. Goldgof, et al. Automatic segmentation of non-enhancing brain tumors in magnetic resonance image. Artif Intell Med, 21 (2001), pp. 43-63.*
Q. Yang and B. Parvin "Harmonic cut and regularized centroid transform for localization of subceullar structures", IEEE Trans. Biomed. Eng., vol. 50, p. 469 , 2003.*
K. L. Zhao et al., "Evaluation of respiratory-induced target motion for esophageal tumors at the gastroesophageal junction", Radiotheraphy and Oncology, vol. 84, No. 3, 2007, pp. 283-289.*
Search Report and Written Opinion for NL 2004470, Aug. 25, 2010.
Marwick et al., "The Future of Cardiovascular Imaging in the Diagnosis and Management of Heart Failure, Part 1: Tasks and Tools," Journal of the American Heart Association, Circulation Cardiovascular Imaging, 2008, pp. 58-69, http://circimaging.ahajournals.org/.
Goldberger et al., "Heart Rhythm Society Scientific Statement on Noninvasive Risk Stratification Techniques for Identifying Patients at Risk for Sudden Cardiac Death," American Heart Association/American College of Cardiology Foundation, vol. 52, No. 14, 2008, pp. 1179-1199.
Klocke et al., "ACC/AHA/ASNC Guidelines for the Clinical Use of Cardiac Radionuclide Imaging—Executive Summary: A Report of the American College of Cardiology/American Heart Association Task Force on Practice Guidelines," Journal of the American Heart Association, Circulation, 2003, pp. 1404-1418, http://circ.ahajournals.org/.
Douglas et al., ACCF/ASE/ACEP/AHA/ASNC/SCAI/SCCT/SCMR 2008 Appropriateness Criteria for Stress Echocardiography: A Report of the American College of Cardiology Foundation Appropriateness Criteria Task Force, American Society of Echocardiography, American College of Emergency Physicians, American Heart Association, American Society of Nuclear Cardiology, Society for Cardiovascular Angiography and Interventions, Society of Cardiovascular Computed Tomography, and Society for Cardiovascular Magnetic Resonance: Endorsed by the Heart Rhythm Soc. & the Soc. of Critical Care Medicine, vol. 51, No. 3, 2008.
Tomlinson et al., "Assessment of Myocardial Viability: Comparison of Echocardiography versus Cardiac Magnetic Resonance Imaging in the Current Era," Heart, Lung and Circulation, 2008, pp. 173-185.
Caiani et al., "Automated Interpretation of Regional Left Ventricular Wall Motion from Cardiac Magnetic Resonance Images," Taylor & Francis Group, LLC, Journal of Cardiovascular Magnetic Resonance, 2006, pp. 427-433.
Nesser et al., "Volumetric analysis of regional left ventricular function with real-time three-dimensional echocardiography: validation by magnetic resonance and clinical utility testing," Heart, 2007, pp. 572-578, http://heart.bmj.com/.
Sugeng et al., "Quantitative Assessment of Left Ventricular Size and Function: Side-by-Side Comparison of Real-Time Three-Dimensional Echocardiography and Computed Tomography With Magnetic Resonance Reference," American Heart Association, Circulation, 2006, pp. 654-661, http://circ.ahajournals.org/.
Sechtem et al., "Regional Left Ventricular Wall Thickening by Magnetic Resonance Imaging: Evaluation in Normal Persons and Patients with Global and Regional Dysfunction," The American Journal of Cardiology, vol. 59, 1987, pp. 145-151.
Park et al., "Assessment of left ventricular asynchrony using volume—time curves of 16 segments by real-time 3 dimensional echocardiography: Comparison with tissue Doppler imaging," The European Journal of Heart Failure, vol. 9, 2007, pp. 62-67.
Aletras et al., "DENSE: Displacement Encoding with Stimulated Echoes in Cardiac Functional MRI," Journal of Magnetic Resonance, vol. 137, 1999, pp. 247-252.
Zerhouni et al. "Human Heart: Tagging with MR Imaging—A Method for Noninvasive Assessment of Myocardlal Motion," Cardiac Radiology, vol. 169, 1988, pp. 59-63.

* cited by examiner

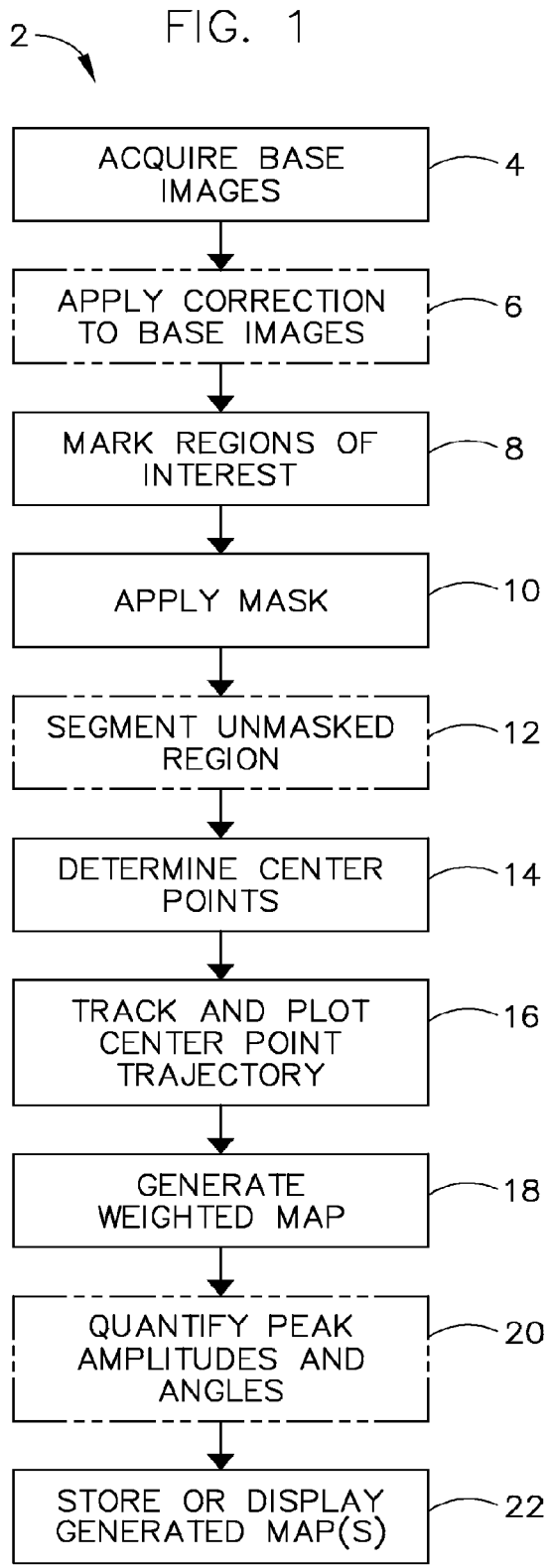

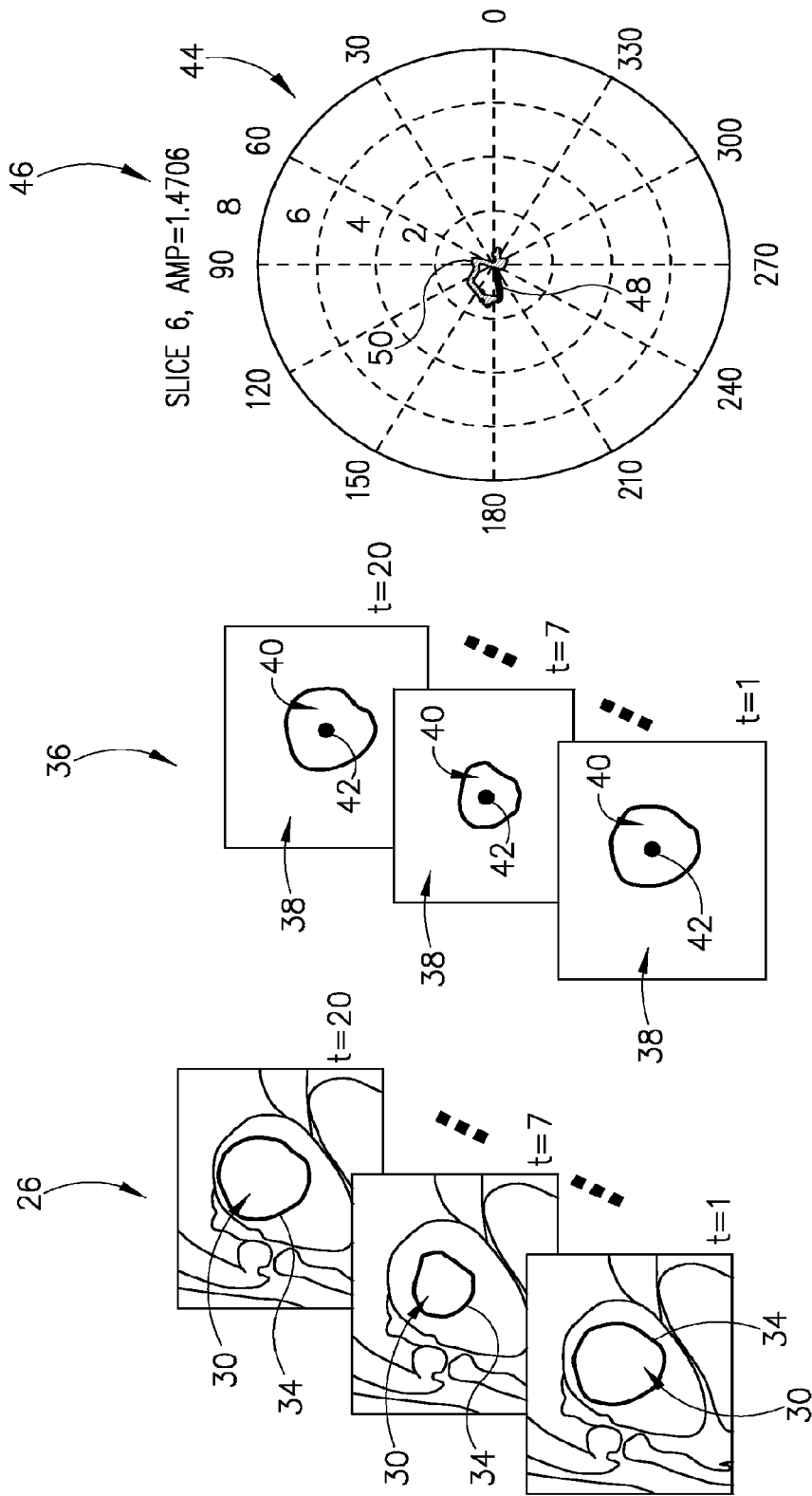

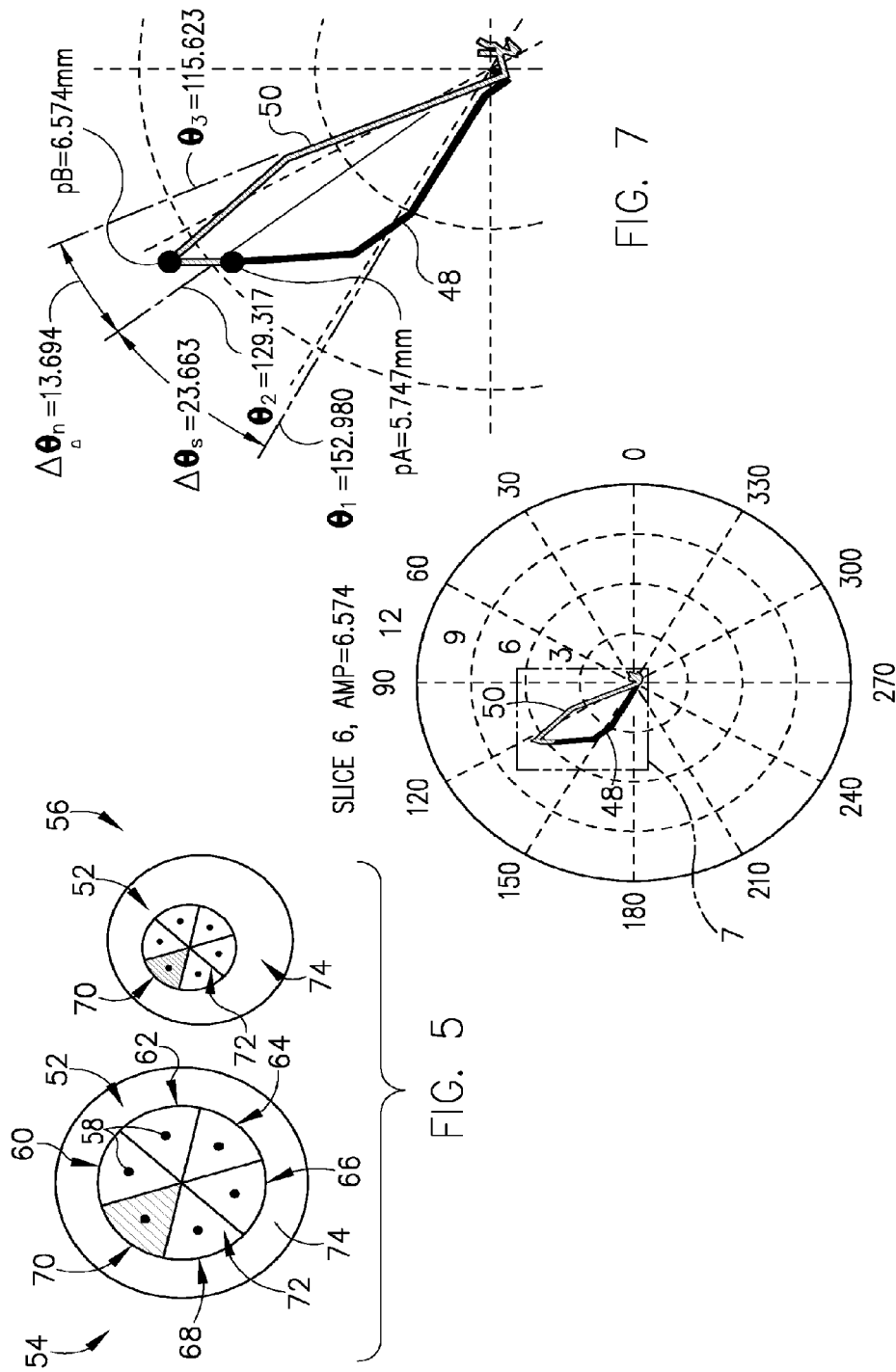

SYSTEM AND METHOD FOR CENTER POINT TRAJECTORY MAPPING

BACKGROUND OF THE INVENTION

The invention relates generally to cavity wall function and, more particularly, to mapping of center point trajectory movement of the cavity.

The assessment of ventricular wall motion is important in patients with suspected or known cardiac disease since it provides quantitative assessment of cardiac function. Ventricular wall motion evaluation is used for clinical decision-making regarding the need for more aggressive medical and/or interventional therapy such as cardiac resynchronization therapy. The non-invasive evaluation of ventricular wall motion is typically performed during rest, exercise, or while under pharmacologic stress and may be based on an imaging modality such as echocardiography, radionuclide imaging, magnetic resonance imaging (MRI), or computed tomography (CT).

Traditional assessments of wall motion during rest or stress include global parameters of left ventricular volumes and ventricular ejection fraction (EF), which is derived from ventricular volume determinations. However, it is not uncommon for patients with mild forms of cardiac disease (e.g., small myocardial infarction) to exhibit only regional wall motion abnormalities while preserving their global parameters (i.e., normal ejection fraction). Detection and quantification of regional wall motion changes are important for early disease detection, surveillance of disease progression, and/or assessment of therapeutic outcome. Regional wall motion analysis is also important for provocative cardiac function testing such as dobutamine stress testing for myocardial viability.

Regional wall motion assessment can be performed visually, but inter- and intra-observer agreement is often less than optimal and highly dependent on reader expertise and experience. More quantitative assessment of regional wall motion can be determined using computer assisted measurement of regional ejection fraction, whereby regional sub-volume ejection fractions are determined, or by measurement of segmental wall thickening. Specific imaging techniques that directly measure the movement of the myocardial wall such as tissue Doppler using echocardiography and specialized MRI pulse sequences (e.g., DENSE or myocardial tagging) are known. These echocardiographic and MR imaging techniques, however, use additional time to acquire specialized data sets and for operator-initiated image post-processing. Some of these quantitative methods can track changes over time and can be used to determine intra- or inter-ventricular mechanical dyssynchrony. Despite the large number of available methods, however, visual assessment (i.e., a qualitative method) of wall motion is still the most widely used, but its application is heavily reliant on observer experience and expertise. Quantitative methods such as those described above are associated with a variety of limitations including prolonged image acquisition times, high observer interactive time and expertise requirements, inherently high spatial and/or temporal resolution requirements, and/or high imaging data/processing requirements.

It would therefore be desirable to have an apparatus and method capable of quantitatively assessing cavity wall motion efficiently while reducing variations in observer-based assessments.

BRIEF DESCRIPTION OF THE INVENTION

According to an aspect of the invention, a computer readable storage medium having stored thereon a computer program comprises instructions, which when executed by a computer, cause the computer to acquire a first plurality of images, each image comprising a masked portion. The instructions also cause the computer to locate a center point of the masked portion in each of the plurality of images and to plot a map based on variances in position of the center points from each other. The instructions further cause the computer to display the map on a display.

According to another aspect of the invention, a method comprises obtaining a plurality of masked images, each masked image comprising an unmasked portion and a masked portion. The method also comprises locating a centroid of the unmasked portion in each of the plurality of masked images and generating a map based on a positional relationship of the centroids to each other. The method further comprises displaying the generated map on a display.

According to yet another aspect of the invention, a computer readable storage medium having stored thereon a computer program comprising instructions, which when executed by a computer, cause the computer to obtain a plurality of images, each image comprising a masked region and an unmasked region. The instructions also cause the computer to locate a center point position of the unmasked region in each of the plurality of images, plot at least one map based on changes in center point positions relative to each other, and display the at least one map to a user.

Various other features and advantages will be made apparent from the following detailed description and the drawings.

BRIEF DESCRIPTION OF THE DRAWINGS

The drawings illustrate embodiments presently contemplated for carrying out the invention.

In the drawings:

FIG. 1 is a flowchart illustrating a technique for center point trajectory mapping according to an embodiment of the invention.

FIGS. 2-4 are schematic diagrams graphically illustrating a portion of the steps of the technique of FIG. 1 according to an embodiment of the invention.

FIG. 5 is a schematic representation of a segmented ROI showing center points for each ROI segment according to an embodiment of the invention.

FIGS. 6 and 7 illustrate exemplary polar maps showing center point movement of a patient with an acute myocardial infarction of the anteroseptal wall of the left ventricle according to an embodiment of the invention.

DETAILED DESCRIPTION

Figure 8:
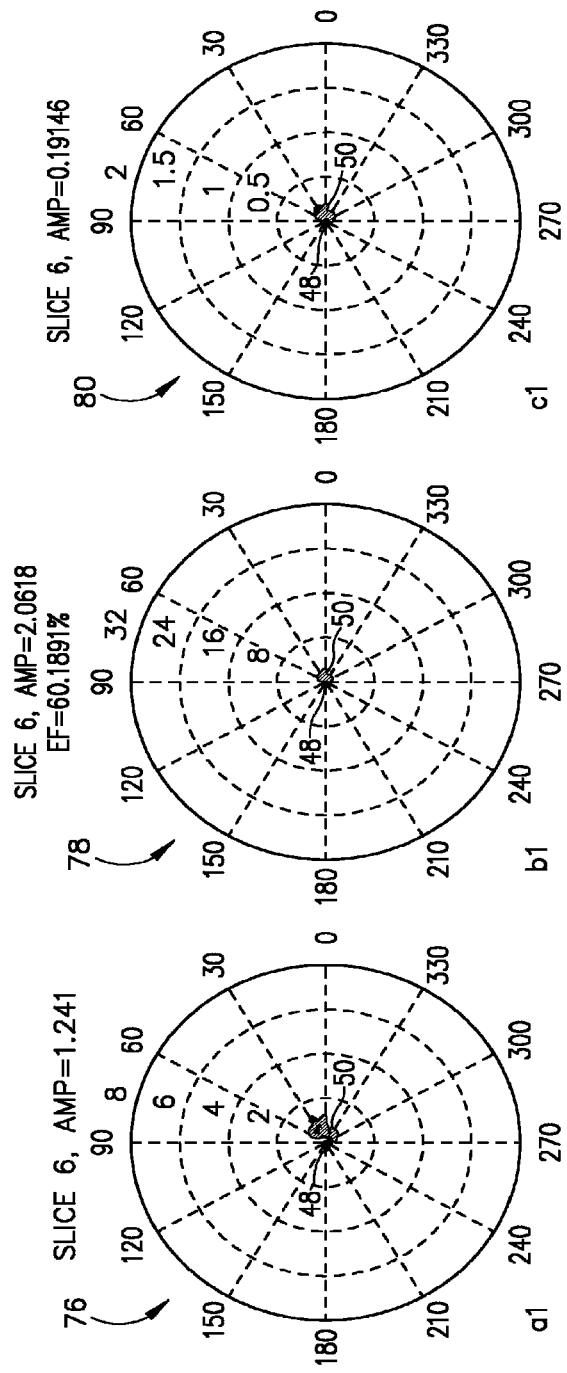
FIG. 8-10 illustrates polar map quantification examples according to an embodiment of the invention.

FIG. 1 shows a technique 2 for center point trajectory mapping according to an embodiment of the invention. The technique 2 may be used to quantify center point trajectory of a cavity. A composite of cavity wall motion, such as ventricular wall motion of a heart, can be summarized during the various cardiac phases of the heart in the movement of the center point of the ventricular chamber throughout the cardiac phases. Technique 2 includes the tracking of the cavity center point over time. In this manner, quantitative measurements such as pattern, angle, and amplitude for regional as well as global wall motion abnormalities may be determined. Changes in center point pattern, angle, and amplitude can be used to assess myocardial response during exercise (e.g., treadmill or hand grip), during pharmacology (e.g., dobutamine or adenosine) stress testing, or following therapeutic intervention (e.g., medication regimen or percutaneous coronary intervention).

Referring to FIGS. 1 and 2, technique 2 includes acquiring a plurality of base images 26 (shown in FIG. 2) at block 4. Acquiring the base images 26 may include performing an imaging scan and reconstructing images from the imaging scan or may include acquiring stored images previously reconstructed. Acquiring stored images allows quantification of center point trajectory movement of a patient without having to re-scan the patient. According to an embodiment of the invention, the base images may be from any imaging modality. For example, the base images may include echocardiography images, radionuclide imaging images, magnetic resonance images, computed tomography images, x-ray images, or ultrasound images. In addition, the base images may be based on any type of scanning sequence or imaging parameter setup. In an embodiment, the plurality of base images are ordered in a consecutive or chronological series of images. For example, cardiac images of a patient may sequentially illustrate ventricular wall motion through a full cardiac cycle (e.g., through the systole and diastole phases). As shown in FIG. 2, images 26 are chronologically ordered and represent twenty, two-dimensional images acquired during a full cardiac cycle. The base images 26 at block 4 may be two-dimensional images or three-dimensional images acquired from an image storage database or acquired in real time. Acquiring images from an image storage database allows any patient images to be used whether the images were recently acquired or were acquired weeks, months, or even years beforehand.

Referring to FIG. 1, a correction may be applied to the base images 26 at block 6 to remove any artifacts that may be present. For example, if the base images are MR images, an inhomogeneity correction may be applied to the base images to correct inhomogeneity artifacts. Other types of corrections may also be applied (e.g., based on the type of imaging modality used to generate the base images) and are contemplated herein. It is also contemplated that a correction may not be applied to the base images if desired. Accordingly, block 6 is shown with dashed lines and may be removed from technique 2 according to an embodiment of the invention.

Referring to FIGS. 1 and 2, a region of interest (ROI) is marked in each of the base images at block 8. The ROIs may be, for example, the left ventricle of a patient's heart as shown in FIG. 2. ROI marking includes delineating a border 34 of a cavity 30 of the ROI in each of the base images 26. ROI marking may include automatically marking the cavities 30 using connected pieces based on signal intensity values of the cavities 30 in the base images. In addition or alternatively thereto, a user may select the respective cavities 30 via computer-aided input.

Referring to FIGS. 1 and 3, at block 10, a mask is applied to each of the base images 26 (shown in FIG. 2). The masks are configured to mask the portions of the base images outside of the delineated border 34 and convert the images into binary mask images 36. FIG. 3 illustrates a masked portion 38 of images 36 masking a region outside the delineated borders 34 of images 26. An unmasked portion 40 of images 36 corresponds to a region inside the delineated borders 34 of images 26.

According to an embodiment of the invention, the unmasked portions 40 of binary mask images 36 may be segmented at block 12 (shown in dashed lines). Segmenting an ROI into multiple segments allows for a more detailed or focal analysis within each ROI as may be desired for a higher spatial definition of movement.

A center point or centroid 42, which is the geometric center of the shape of the unmasked portions 40, is determined or calculated for each unmasked portion 40 or segmented portion in the binary mask images 36 at block 14. According to an embodiment of the invention, calculated center points 42 from the binary mask images 36 are used for center point tracking.

Referring to FIGS. 1, 3, and 4, trajectories of the center points 42 between consecutive images 36 are tracked and plotted at block 16. Tracking of the center point trajectories includes determining the differences in center point positions between the respective consecutive images 36. These differences identify an amplitude of center point movement and an angle of center point movement. Plotting of the center point trajectories includes plotting the distances (amplitudes) and directions (angles) of center point trajectory movement on a polar coordinate map 44. Polar coordinate map 44 shown in FIG. 4 is an absolute center point displacement map showing raw or absolute values for the center point trajectory data. The plotting of amplitudes and angles of center point movement on the map illustrates, for example, the degree of wall motion abnormality and the location indicated by direction in both systolic and diastolic phases of a cardiac phase. The plotting of amplitudes and angles of center point movement on the map also illustrates center point trajectory patterns useful in diagnoses.

Referring to FIG. 1, post-processing of map data includes generating a weighted center point displacement map at block 18 based on the absolute center point displacement map created at block 16. In one embodiment, the weighted center point displacement map is an ejection fraction (EF) weighted center point displacement map that is generated by calculating a local EF value based on the base images and dividing the absolute center displacement by the local EF value. In this manner, a quantitative tool for assessment and surveillance of patients with diffuse wall motion abnormalities may be generated. For example, a patient with global heart disease may have small absolute displacement as identified on the absolute center point displacement map, but the EF will be low. Accordingly, the ejection fraction weighted center point displacement map may be used to assess and quantify issues related to ejection fraction.

In another embodiment, the weighted center point displacement map is a chamber radius change weighted center point displacement map useful for global cardiac motion evaluation that is generated by calculating a difference between a maximum radius of the ROIs and a minimum radius of the ROIs among all the images (e.g., in the whole cardiac cycle) and dividing absolute center point displacement by the calculated difference. As such, an additional quantitative tool for assessment and surveillance of patients is provided.

Referring to FIGS. 1 and 4, in an embodiment of the invention, post-processing of map data also includes identifying a peak or maximum amplitude 46 of center point movement in the absolute or weighted center point displacement maps and displaying the peak amplitude 46 with its respective map at block 20 (shown with dashed lines). The peak amplitude 46 represents the largest distance difference between the beginning or first center point and any of the other center points. In addition, the number of the image or slice where the peak amplitude occurs may be identified and displayed. Furthermore, it is contemplated that a peak or maximum angle may also be identified and displayed based on a largest angular difference between the first center point and any of the other center points.

As shown in FIG. 4, a peak amplitude of 1.4706 has been identified from the data in map 44 and is displayed, while the slice number (six) where the peak amplitude occurs has also been identified and displayed. The time point of peak amplitude in this case corresponds to the time point of end-systole and can serve as a measure of degree wall motion defect not only in terms of amplitude and angle but also time. Identification of the maximum amplitude of center point movement in this manner allows for computer-related quantification and reduces guessing introduced by visual assessment.

The absolute or weighted center point displacement maps and their related data generated at blocks 18-20 may be stored for later use or displayed to a user on a display at block 22. According to an embodiment of the invention, the map display includes color-coding separate portions of center point movement among the ROIs. For example, movement of the center points during a systolic phase 48 (shown in FIG. 4 and similarly labeled in FIGS. 6-10) of a cardiac cycle may be displayed in one line style and/or color such as red, and movement of the center points during a diastolic phase 50 (shown in FIG. 4 and similarly labeled in FIGS. 6-10) of the cardiac cycle may be displayed in another line style and/or color such as blue. In this manner, motion abnormality in the two phases can be uncoupled.

Besides amplitudes and angles, the pattern of the trajectory is also useful. For example, the shape or the pattern of the trajectory can be used for dyssynchrony evaluation. That is, the distance between the systolic phase 48 and the diastolic phase 50 indicate a degree of dyssynchronization. In general, the wider the distance between systolic and diastolic trajectories, the more the possibility of a dyssynchronized cardiac motion exists.

FIG. 5 is a schematic representation of a segmented ROI showing center points for each ROI segment according to an embodiment of the invention. In FIG. 5, a segmented ROI 52 of two cardiac phases 54, 56 is shown that shows center points 58 for each ROI segment 60, 62, 64, 66, 68, 70 according to an embodiment of the invention. Segmenting an ROI into multiple local segments 60-70 allows for a more detailed or focal analysis within each ROI as may be desired for a higher spatial definition of movement. Segmented ROI 52 may be identified and segmented according to that described above in FIG. 1 with respect to blocks 4-16. Cardiac phase 54 illustrates a relaxed state and includes a chamber 72 surrounded by cardiac muscle 74, which is shown having a uniform thickness about chamber 72. ROI segments 60-70 are distributed throughout chamber 72. In cardiac phase 56, a contracted state (i.e., end-systole) is illustrated. Cardiac phase 56 illustrates that the segmented ROI 52 is shifted in the direction of ROI segment 70. Accordingly, the direction of abnormal wall motion is also in the direction of ROI segment 70. While FIG. 5 shows six segments in segmented ROI 52, it is contemplated that any number of segments may be used. By comparing regional center point trajectories, relative time points for peak amplitude can be compared for determination of ventricular dyssynchrony (i.e., the condition in which ventricular wall motion is no longer synchronous in the time domain). In addition to comparing regional center point trajectories, the global center point trajectories of the left and right ventricles (or of any other chambers) may also be compared to determine cardiac dyssynchrony in the time domain as well as in their relative motions. In this manner, a comparison of regional or global center point trajectory over time will enable the quantification and assessment of changes in amplitude over time, differences in trajectory arc over time, and changes in trajectory pattern over time between various time points.

Abnormal wall motion is determined by high amplitude (e.g., greater than 3.0) of absolute movement of the center point towards the region of abnormal wall motion. FIGS. 6 and 7 are examples of movement of the center point shown in polar maps of a patient with an acute myocardial infarction of the anteroseptal wall of the left ventricle for illustrative purposes according to one embodiment of the invention. FIG. 7 shows a close-up of the polar map of FIG. 6 about line 7-7. According to an embodiment of the invention, angles and amplitudes relevant to the polar map may be quantified and shown. A series of angles $\theta1$, $\theta2$, and $\theta3$ are quantified and displayed as well as a difference between $\theta2$ and $\theta1$ ($\Delta\theta s = \theta2 - \theta1$) and a difference between $\theta3$ and $\theta2$ ($\Delta\theta_D = \theta3 - \theta2$), where $\Delta\theta s$ is an angle of trajectory during systolic contraction (i.e., systole), and $\Delta\theta_D$ is an angle of trajectory diastolic relaxation (i.e., diastole) of the left ventricle. After end of systolic phase 48 where there is a minimal chamber volume, an amplitude $\rho$ at point A is 5.747 mm. When the amplitude $\rho$ reaches the peak at point B, it is in diastolic phase 50. The shapes of the systolic and diastolic phases 48, 50 indicate that wall motion is not synchronized as there is increased amplitude of the center point despite the overall chamber volume reaching a minimum (i.e., end-systole). The width of the arcs, $\Delta\theta s$, $\Delta\theta D$, and $\Delta\theta s + \Delta\theta D = 37.357°$, are also indicators of how dyssynchronized the motion is. The angle and amplitude of the center point trajectory can be used to follow left ventricular remodeling and functional recovery over time. As shown in FIGS. 6 and 7, a peak amplitude, a trajectory direction, a trajectory pattern, and a trajectory temporal arc corresponding to center point movement over time may be quantified according to embodiments of the invention.

Figure 9:
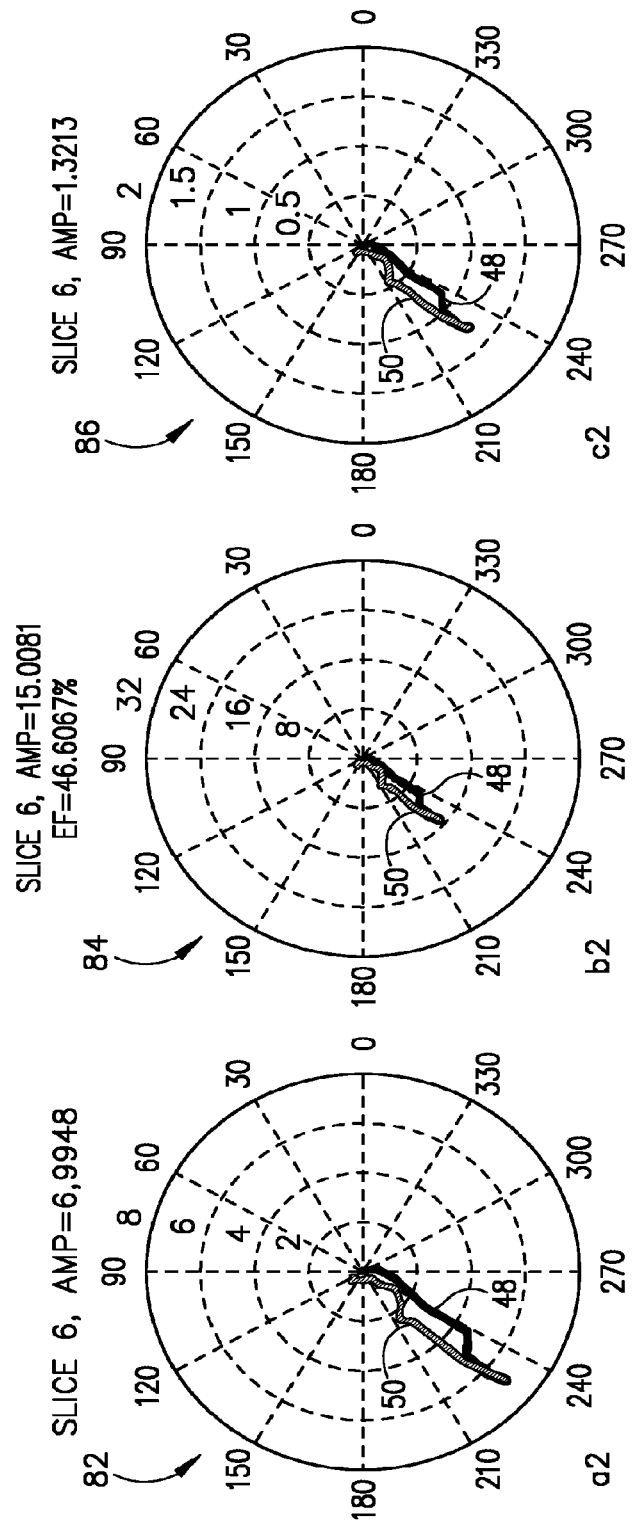
Figure 10:
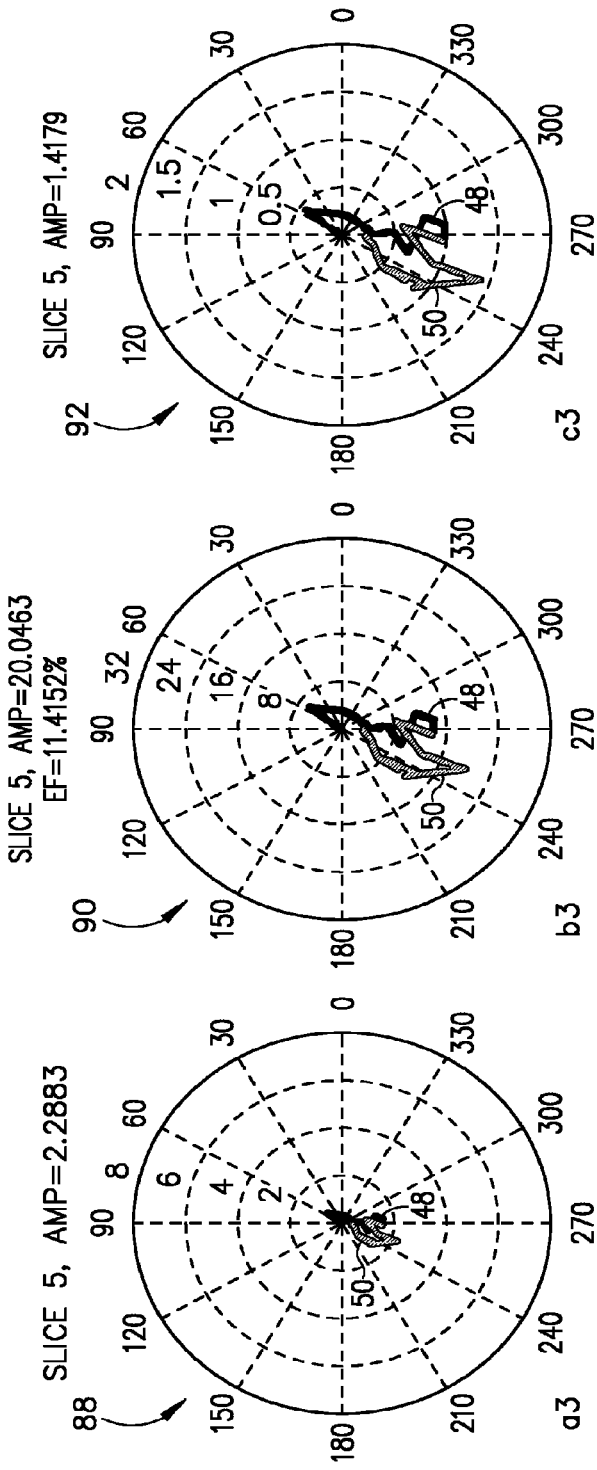

FIGS. 8-10 illustrates polar map quantification examples according to an embodiment of the invention. Maps 76, 78, and 80 respectively illustrate absolute (or raw), EF weighted, and chamber radius change weighted displacement center point maps of a healthy left ventricle. Maps 82, 84, and 86 respectively illustrate absolute (or raw), EF weighted, and chamber radius change weighted displacement center point maps of a left ventricle with hypokinesis in the inferoseptal wall. Maps 88, 90, 92 respectively illustrate absolute (or raw), EF weighted, and chamber radius change weighted displacement center point maps of a left ventricle with global hypokinesis. Absolute center point map 76 displays low amplitude movement of the center point trajectory. On EF weighted map 78 and radius change weighted map 80, low or little amplitude movement of the respective center point trajectories for the healthy left ventricle are shown. In maps 82-86, the amplitude movement is substantially larger than that shown in maps 76-80. As stated above, maps 88-92 show maps of a left ventricle with global hypokinesis. Although in absolute displacement generate weighted map 88 the amplitude movement is less than 3.0, the EF map 90 and the chamber radius weighted map 92 show that there is a substantial deviation of the center points that can be measured in pattern, angle, and amplitude. Accordingly, it can be understood that the EF and radius change weighted maps provide extra information for diagnosis for both regional and global wall motion abnormalities in addition to the information of the absolute map.

Figure 11:
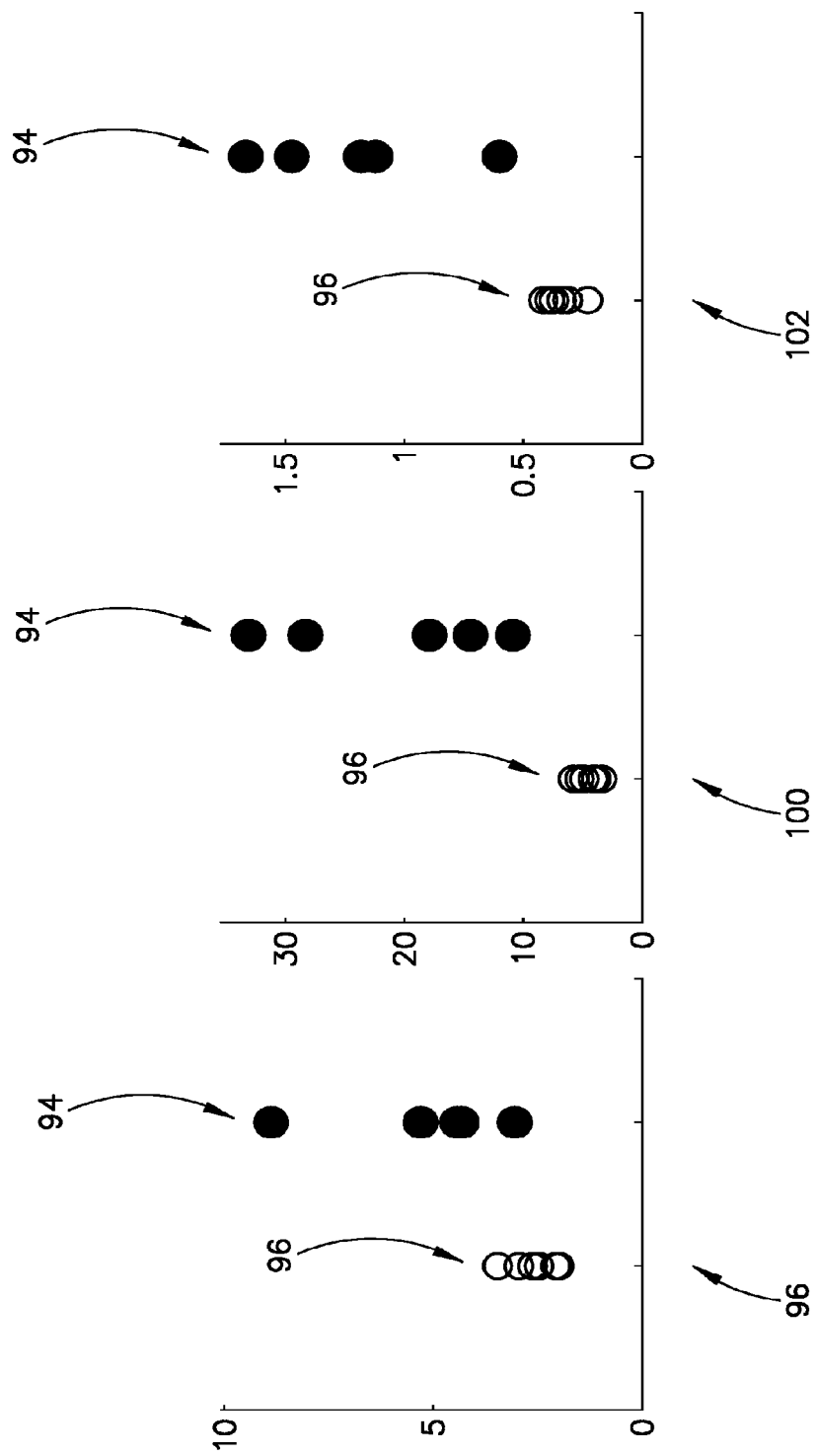
FIG. 11 illustrates exemplary plots of patient data using Welch two-sample t-test according to an embodiment of the invention.

FIG. 11 illustrates plots of patient data using Welch two-sample t-test. A first group of patient data 94 for patients with mild to severe global hypokinesis is illustrated together with a second group of patient data 96 for healthy subjects. A first plot 98 illustrates data related to absolute amplitudes as quantified according to an embodiment of the invention. As illustrated, the patient data 88 for the healthy subjects all have amplitudes below five. The patient data 86 for patients with hypokinesis, however, have mixed amplitudes—including amplitudes also below 5.0. Accordingly, setting a diagnosis threshold based solely on the absolute amplitude center point trajectories may not separate the healthy subjects from all the patients with mild to severe global hypokinesis.

A second plot 100 and a third plot 102 respectively illustrate data related to EF weighted amplitudes and to chamber radius change weighted amplitudes as quantified according to an embodiment of the invention. The data 88 for healthy subjects in plots 100, 102 are shown more separated from the data 86 for subjects with such as, for example, 10.0 and 0.5, respectively, for the EF weighted plot 100 and the chamber radius change weighted plot 102 may improve accuracy in diagnosing patients with wall motion abnormalities.

Figure 12:
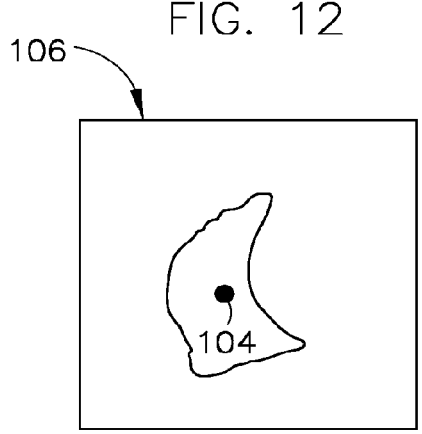
FIG. 12 illustrates a right ventricle ROI binary mask image according to an embodiment of the invention.

FIG. 12 illustrates a right ventricle ROI binary mask image according to an embodiment of the invention. In FIG. 12, a center point 104 is shown that was calculated for a right ventricle ROI in a binary mask image 106 of a patient's heart. The technique as described above may be used to track the center points of images for other cardiac chambers (e.g., the right ventricle (as shown in FIG. 12), the left atrium, the right atrium). The technique described above may also be used to track center points for ROIs of other hollow chambers such as an esophagus or a stomach of an imaging subject. In addition, it is contemplated that the ROIs may be of any cavity of an imaging subject or object in either a medical or a non-medical setting. Furthermore, the desired ROI cavity may have an irregular shape as illustrated in FIG. 12.

As described above, the base images having the desired ROIs may include images selected from any type of modality including: echocardiography images, radionuclide imaging images, magnetic resonance images, computed tomography images, x-ray images, or ultrasound images based on any type of scanning sequence or imaging parameter setup. It is contemplated that diagnosis of wall motion abnormalities can include the quantification of cavity wall motion abnormalities from one modality compared with the quantification of the cavity wall motion abnormalities from a different modality. Further, as center point measurements are quantitative, direct comparison of wall motion between different patients is also contemplated.

Figure 13:
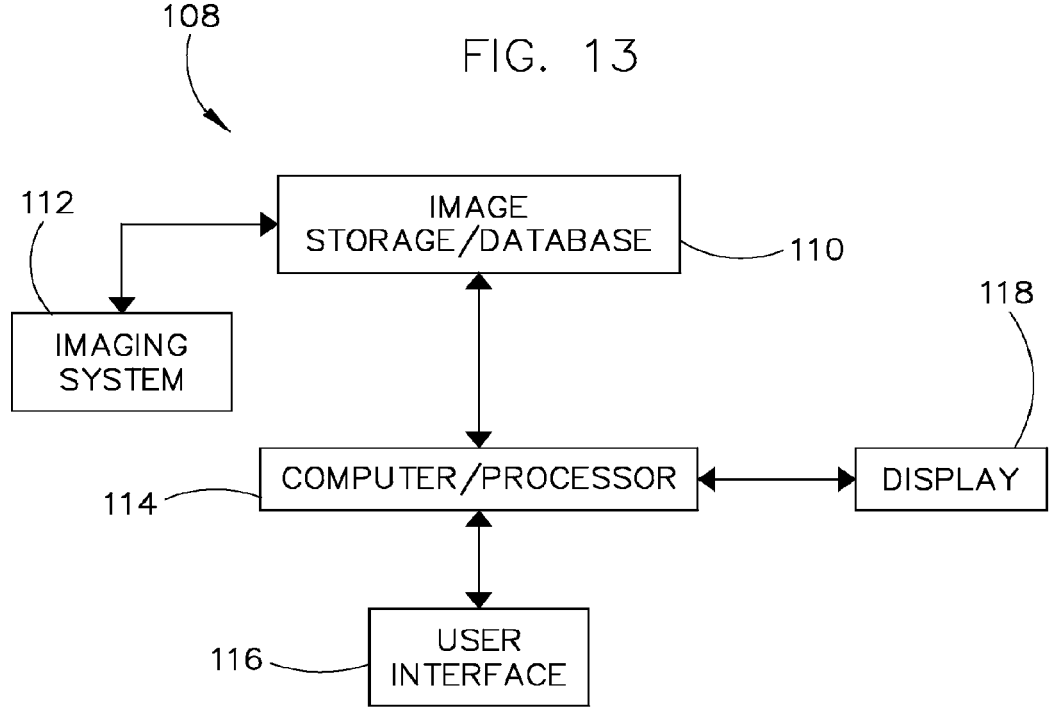
FIG. 13 is a schematic block diagram of an exemplary system incorporating an embodiment of the invention.

FIG. 13 is a schematic block diagram of an exemplary system 108 incorporating an embodiment of the invention as an example. System 108 includes an image storage or database 110 configured to store images received from an imaging system 112, for example. According to embodiments of the invention, imaging system 112 is a system capable of imaging an object via any type of modality including magnetic resonance imaging, computed tomography imaging, x-ray imaging, ultrasound imaging, or the like. In addition, images generated by imaging system 112 and stored in image database 110 may be based on any type of scanning sequence or imaging parameter setup A computer or processor 114 is programmed based on embodiments of the invention such as technique 2 described above with respect to FIG. 1. A user interface 116 allows the computer/processor 114 to receive user instructions such as instructions regarding which images to acquire from database 110 and instructions regarding choosing of the ROI cavities as described above, for example. A display 118 coupled to computer/processor 114 visually depicts any polar maps generated from the images via the computer/processor 114. Additionally, the computer/processor 114 may be programmed to quantify, compare, and display regional or global center point trajectory changes in amplitude over time, differences in trajectory arc over time, and changes in trajectory pattern over time between various time points.

Figure 14:
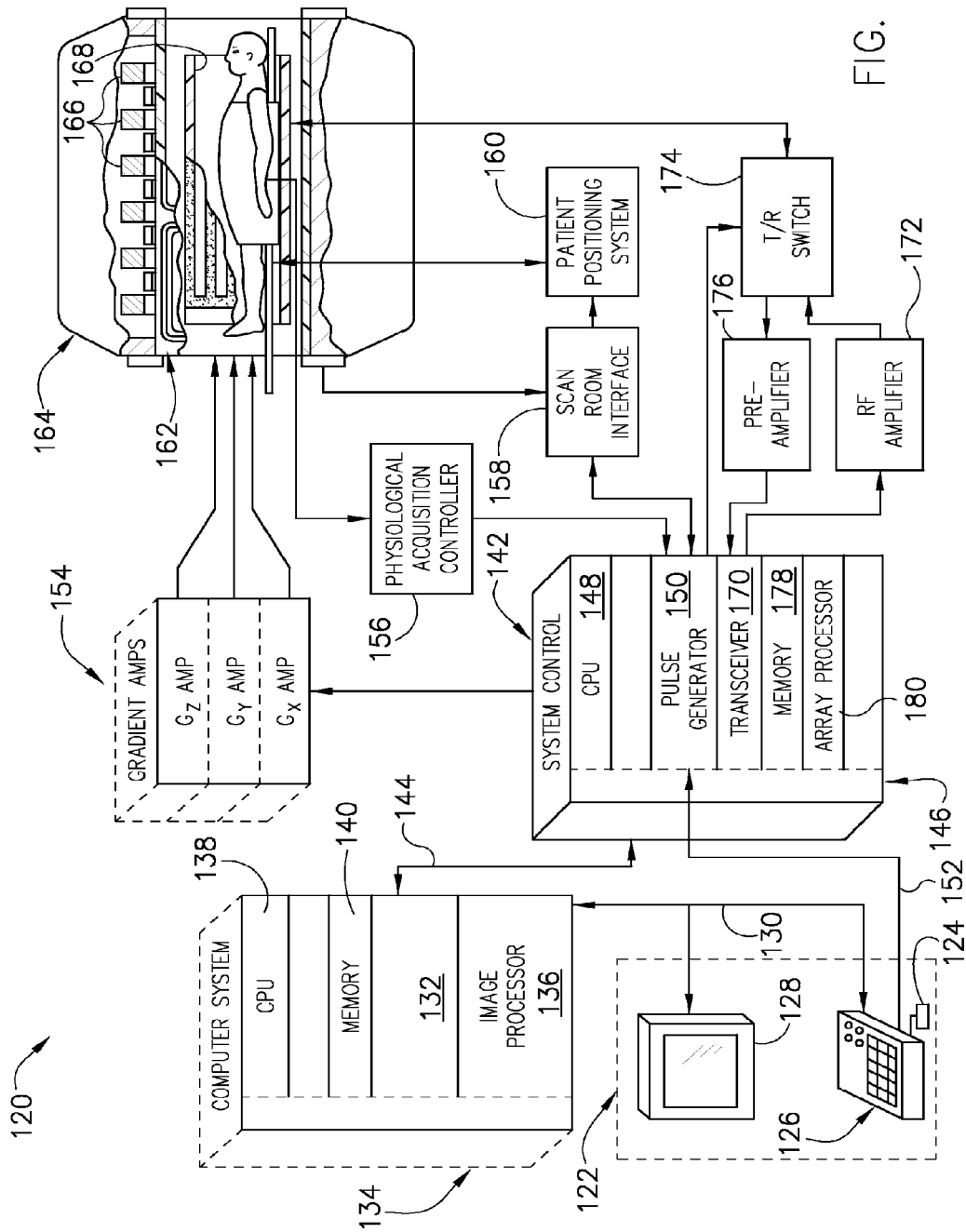
FIG. 14 is a schematic block diagram of an exemplary MR imaging system incorporating an embodiment of the invention.

While embodiments of the invention include acquiring images from any of a multiple of imaging modalities, FIG. 14 illustrates the major components of a magnetic resonance imaging (MRI) system 120 incorporating an embodiment of the invention as an example. The operation of the system 120 is controlled from an operator console 122, which includes a keyboard or other input device 124, a control panel 126, and a display screen 128. The console 122 communicates through a link 130 with a separate computer system 132 that enables an operator to control the production and display of images on the display screen 128. The computer system 132 includes a number of modules which communicate with each other through a backplane 134. These include an image processor module 136, a CPU module 138 and a memory module 140 that may include a frame buffer for storing image data arrays. The computer system 132 communicates with a separate system control 142 through a high speed serial link 144. The input device 124 can include a mouse, joystick, keyboard, track ball, touch activated screen, light wand, voice control, or any similar or equivalent input device, and may be used for interactive geometry prescription.

The system control 142 includes a set of modules connected together by a backplane 146. These include a CPU module 148 and a pulse generator module 150 which connects to the operator console 122 through a serial link 152. It is through link 152 that the system control 142 receives commands from the operator to indicate the scan sequence that is to be performed. The pulse generator module 150 operates the system components to carry out the desired scan sequence and produces data which indicates the timing, strength and shape of the RF pulses produced, and the timing and length of the data acquisition window. The pulse generator module 150 connects to a set of gradient amplifiers 154, to indicate the timing and shape of the gradient pulses that are produced during the scan. The pulse generator module 150 can also receive patient data from a physiological acquisition controller 156 that receives signals from a number of different sensors connected to the patient, such as ECG signals from electrodes attached to the patient. And finally, the pulse generator module 150 connects to a scan room interface circuit 158 which receives signals from various sensors associated with the condition of the patient and the magnet system. It is also through the scan room interface circuit 158 that a patient positioning system 160 receives commands to move the patient to the desired position for the scan.

The gradient waveforms produced by the pulse generator module 150 are applied to the gradient amplifier system 154 having Gx, Gy, and Gz amplifiers. Each gradient amplifier excites a corresponding physical gradient coil in a gradient coil assembly generally designated 162 to produce the magnetic field gradients used for spatially encoding acquired signals. The gradient coil assembly 162 forms part of a resonance assembly 164 which includes a polarizing magnet 166 and a whole-body RF coil 168. A transceiver module 170 in the system control 142 produces pulses which are amplified by an RF amplifier 172 and coupled to the RF coil 168 by a transmit/receive switch 174. The resulting signals emitted by the excited nuclei in the patient may be sensed by the same RF coil 168 and coupled through the transmit/receive switch 174 to a preamplifier 176. The amplified MR signals are demodulated, filtered, and digitized in the receiver section of the transceiver 170. The transmit/receive switch 174 is controlled by a signal from the pulse generator module 150 to electrically connect the RF amplifier 172 to the coil 168 during the transmit mode and to connect the preamplifier 176 to the coil 168 during the receive mode. The transmit/receive switch 174 can also enable a separate RF coil (for example, a surface coil) to be used in either the transmit or receive mode.

The MR signals picked up by the RF coil 168 are digitized by the transceiver module 170 and transferred to a memory module 178 in the system control 142. A scan is complete when an array of raw k-space data has been acquired in the memory module 178. This raw k-space data is rearranged into separate k-space data arrays for each image to be reconstructed, and each of these is input to an array processor 180, which operates to Fourier transform the data into an array of image data. This image data is conveyed through the serial link 144 to the computer system 132 where it is stored in memory. In response to commands received from the operator console 122, this image data may be archived in long term storage or it may be further processed by the image processor 136 and conveyed to the operator console 122 and presented on the display 128.

The computer system 132 is programmed to quantify and display maps of center point trajectory movement as described above according to an embodiment of the invention. The computer system 132 may retrieve stored images from historical scans or may acquire images during a scan followed thereafter by quantification of center point trajectories and map generation and display as described above according to an embodiment of the invention.

A technical contribution for the disclosed method and apparatus is that it provides for a computer implemented mapping of center point trajectory movement of a cavity.

Therefore, according to an embodiment of the invention, a computer readable storage medium having stored thereon a computer program comprises instructions, which when executed by a computer, cause the computer to acquire a first plurality of images, each image comprising a masked portion. The instructions also cause the computer to locate a center point of the masked portion in each of the plurality of images and to plot a map based on variances in position of the center points from each other. The instructions further cause the computer to display the map on a display.

According to another embodiment of the invention, a method comprises obtaining a plurality of masked images, each masked image comprising an unmasked portion and a masked portion. The method also comprises locating a centroid of the unmasked portion in each of the plurality of masked images and generating a map based on a positional relationship of the centroids to each other. The method further comprises displaying the generated map on a display.

According to yet another embodiment of the invention, a computer readable storage medium having stored thereon a computer program comprising instructions, which when executed by a computer, cause the computer to obtain a plurality of images, each image comprising a masked region and an unmasked region. The instructions also cause the computer to locate a center point position of the unmasked region in each of the plurality of images, plot at least one map based on changes in center point positions relative to each other, and display the at least one map to a user.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A non-transitory computer readable storage medium having stored thereon a computer program comprising instructions, which when executed by a computer, cause the computer to:
   acquire a first plurality of images, each image comprising a masked portion and an unmasked portion;
   locate a center point of the unmasked portion in each of the plurality of images;
   plot a map based on variances in position of the center points from each other on a polar coordinate map;
   quantify a motion abnormality of a wall of the unmasked portion over time; and
   display the map and the quantified motion abnormality on a display.

2. The computer readable storage medium of claim 1 having further instructions to cause the computer to:
   acquire a second plurality of images acquired via an imaging scanner;
   mark a region of interest (ROI) in each image of the second plurality of images based on signal intensity values of the ROI; and
   apply a mask to a portion of each image of the second plurality of images outside of the marked ROIs.

3. The computer readable storage medium of claim 2 having further instructions to cause the computer to apply an artifact correction to each of the second plurality of images.

4. The computer readable storage medium of claim 2 wherein the second plurality of images is one of a plurality of echocardiography images, a plurality of radionuclide imaging images, a plurality of magnetic resonance images, a plurality of computed tomography images, a plurality of x-ray images, and a plurality of ultrasound images.

5. The computer readable storage medium of claim 1 wherein the instructions that cause the computer to plot the map cause the computer to plot differences in positions of the center points between consecutive images of the first plurality of images onto a polar coordinate map.

6. The computer readable storage medium of claim 5 wherein the instructions that cause the computer to plot the differences cause the computer to plot distances and directions of the positions of the center points between consecutive images of the first plurality of images.

7. The computer readable storage medium of claim 1 having further instructions to cause the computer to:
   identify a peak distance difference between a center point of one image of the first plurality of images and a center point of any other image of the first plurality of images; and
   display the peak distance difference on the map.

8. The computer readable storage medium of claim 1 wherein the ROI of each image of the first plurality of images corresponds to one of a left ventricle, a right ventricle, an esophagus, and a stomach of an imaging subject.

9. The computer readable storage medium of claim 1 wherein the masked portion of each image of the first plurality of images comprises an irregular shape.

10. The computer readable storage medium of claim 1 having further instructions to cause the computer to convert the map into one of an ejection fraction weighted center point map and a chamber radius change weighted center point map.

11. The computer readable storage medium of claim 1 having further instructions to cause the computer to display systolic movement variances of the center points differently than diastolic movement variances of the center points on the map.

12. A method comprising:
acquiring MR imaging data from an imaging subject during an MR imaging scan;
reconstructing the MR imaging data into a plurality of anatomical images;
generating a plurality of masked images based on the plurality of anatomical images, each masked image comprising an unmasked portion and a masked portion;
locating a centroid of the unmasked portion in each of the plurality of masked images;
generating a map based on a positional relationship of the centroids to each other;
quantifying a deformation of the unmasked portion over time;
displaying the generated map and deformation on a display; and
wherein generating the map comprises calculating a distance of centroid movement and a direction of centroid movement between the centroids of consecutive images of the plurality of masked images on a polar coordinate map.

13. The method of claim 12 wherein generating a plurality of masked images comprises:
obtaining the plurality of anatomical images comprising a region of interest (ROI);
delineating a border of the ROI in each of the plurality of unmasked images; and
converting the plurality of unmasked images to the plurality of masked images via a binary mask based on the delineated borders, the binary mask configured to mask regions of the plurality of unmasked images outside the delineated borders.

14. The method of claim 12 further comprising:
identifying a peak distance difference between a center point of one image of the plurality of masked images and a center point of any other image of the plurality of masked images; and
displaying the peak distance difference on the display.

15. A non-transitory computer readable storage medium having stored thereon a computer program comprising instructions, which when executed by a computer, cause the computer to:
obtain a plurality of images, each image comprising a masked region and an unmasked region;
locate a center point position of the unmasked region in each of the plurality of images;
plot at least one map based on changes in center point positions relative to each other on a polar coordinate map;
quantify a wall motion abnormality of the unmasked region over time; and
display the at least one map and the quantified wall motion abnormality to a user.

16. The computer readable storage medium of claim 15 wherein plotting the at least one map comprises:
plotting an absolute center point displacement map; and
wherein the computer is further programmed to quantify a peak amplitude, a trajectory direction, a trajectory pattern, and a trajectory temporal arc corresponding to center point movement over time based on the absolute center point displacement map.

17. The computer readable storage medium of claim 15 wherein plotting the at least one map comprises:
plotting an ejection fraction weighted center point displacement map; and
wherein the computer is further programmed to quantify a peak amplitude corresponding to center point movement based on the ejection fraction weighted center point displacement map.

18. The computer readable storage medium of claim 15 wherein plotting the at least one map comprises:
plotting a chamber radius change weighted center point displacement map; and
wherein the computer is further programmed to quantify a peak amplitude corresponding to center point movement based on the chamber radius change weighted center point displacement map.

19. The computer readable storage medium of claim 15 wherein acquiring comprises acquiring one of a plurality of medical images and a plurality of non-medical images.

20. The computer readable storage medium of claim 15 wherein the computer is further programmed to quantify and compare center point trajectory changes between various time points, wherein the center point trajectory changes comprise one of changes in amplitude over time, differences in trajectory arc over time, and changes in trajectory pattern over time.

* * * * *